United States Patent
Seitz

(10) Patent No.: US 10,111,829 B2
(45) Date of Patent: Oct. 30, 2018

(54) PROBIOTIC-CONTAINING ANIMAL SHAMPOO AND METHODS OF USE

(71) Applicant: Alpha Tech Pet, Inc., Littleton, MA (US)

(72) Inventor: Shawn E. Seitz, Carlisle, MA (US)

(73) Assignee: Alpha Pet Tech, Inc., Littleton, MA (US)

(*) Notice: Subject to any disclaimer, the term of this patent is extended or adjusted under 35 U.S.C. 154(b) by 0 days.

(21) Appl. No.: 15/910,275

(22) Filed: Mar. 2, 2018

(65) Prior Publication Data

US 2018/0250223 A1 Sep. 6, 2018

Related U.S. Application Data

(60) Provisional application No. 62/466,418, filed on Mar. 3, 2017.

(51) Int. Cl.
| | |
|---|---|
| *A61K 35/66* | (2015.01) |
| *A61K 8/99* | (2017.01) |
| *A61K 9/00* | (2006.01) |
| *A61Q 5/02* | (2006.01) |
| *A61K 35/741* | (2015.01) |
| *A61K 35/00* | (2006.01) |

(52) U.S. Cl.
CPC .............. *A61K 8/99* (2013.01); *A61K 9/0053* (2013.01); *A61K 35/741* (2013.01); *A61Q 5/02* (2013.01); *A61K 2035/11* (2013.01)

(58) Field of Classification Search
CPC ..................................................... A61K 35/66
See application file for complete search history.

(56) References Cited

U.S. PATENT DOCUMENTS

| 9,265,719 B2 | 2/2016 | Castiel et al. |
| 2010/0273239 A1 | 10/2010 | Flambard |

OTHER PUBLICATIONS

Skout's Honor, Skout's Honor Probiotic Shampoo & Conditioner (2-in-1), Lavender, https://www.skoutshonor.com/collections/grooming/products/probiotic-shampoo-conditioner-2-in-1, undated ref.*

Skout's Honor, U.S. Trademark Reg. No. 4,871,789, registered on Dec. 15, 2015.*

* cited by examiner

*Primary Examiner* — Rosanne Kosson
(74) *Attorney, Agent, or Firm* — Elmore Patent Law Group, P.C.; Darlene Vanstone; Carolyn Elmore

(57) ABSTRACT

The present invention provides a probiotic-containing animal shampoo and methods of using a probiotic-containing animal shampoo for cleansing, conditioning and deodorizing an animal's fur or hair and for supporting digestive health in the animal after the animal orally ingests the probiotic deposited by the shampoo during the animal's oral self-grooming of its fur or hair. The methods of the invention are particularly useful for administering probiotics to an animal, preferably a dog.

14 Claims, No Drawings

PROBIOTIC-CONTAINING ANIMAL SHAMPOO AND METHODS OF USE

RELATED APPLICATION

This application claims the benefit of U.S. Provisional Application No. 62/466,418, filed on Mar. 3, 2017. The entire teachings of the above application are incorporated herein by reference.

BACKGROUND OF THE INVENTION

The intestinal tract plays a critical role in animal health and wellness. To help fulfill this role, the intestinal tract contains various microorganisms that comprise a healthy gastrointestinal microflora under normal conditions. The microflora confers many benefits to the animal, e.g., the production of fatty acids that fuel the cells that line the gastrointestinal lumen, the synthesis of vitamins, and the synthesis of enzymes that aid in the breakdown and digestion of food. In addition, the microflora aids the immune system in host protection from disease. For example, microflora are known to inhibit the attachment to and colonization of potential pathogens within the gastrointestinal tract and to stimulate the production of cytokines and immunoglobulins.

Probiotics and their benefits for non-human animal health are well known to skilled artisans. Probiotics are live microorganisms that have a beneficial effect in the prevention and treatment of specific medical conditions when ingested. Probiotics are believed to exert biological effects through a phenomenon known as colonization resistance. Probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Probiotics are known to enhance intestinal function, stimulate the immune system, reduce inflammation, and diminish the population of harmful microorganisms in the gastrointestinal tract.

While probiotics are generally useful for promoting the health of a non-human animal, they are often difficult to orally administer to the animal. Often, the palatability must be disguised or enhanced using other compounds or compositions. There is, therefore, a need for new compositions containing probiotics.

SUMMARY OF THE INVENTION

The present invention provides a probiotic-containing animal shampoo and methods of using a probiotic-containing animal shampoo for cleansing, conditioning and deodorizing an animal's fur or hair and for supporting digestive health in the animal after the animal orally ingests the probiotic deposited by the shampoo during the animal's oral self-grooming of its fur or hair. The methods of the invention are particularly useful for administering probiotics to an animal, preferably a dog.

DETAILED DESCRIPTION OF THE INVENTION

The terms "a", "an" and "the" as used herein are defined to mean "one or more" and include the plural unless the context is inappropriate.

The term "comprising" as used herein which is synonymous with "including," "containing," or "characterized by," is inclusive or open-ended and does not exclude additional, unrecited elements of a composition or method steps. The term "consisting of" excludes any element, step, or ingredient that is not otherwise specified. The term "consisting essentially of" limits the scope of a composition or method to the specified materials or steps and those that do not materially affect the basic and novel characteristic(s) of the specified composition or method.

As used herein, the term "animal" encompasses all non-human animals including domestic and wild animals, such as non-human primates, farm animals, companion animals, marine animals, zoo animals, fur bearing animals, exotic animals, etc. Preferred animals self-groom by licking their coats and/or skin. The invention relates particularly to horses, cats and most preferably to dogs.

The term "probiotic" means any microorganism that exerts a beneficial effect on the host animal such as increased health or resistance to disease. Probiotics can exhibit one or more of the following non-limiting characteristics: non-pathogenic or non-toxic to the host; are present as viable cells, preferably in large numbers; capable of survival, metabolism, and persistence in the gut environment (e.g., resistance to low pH and gastrointestinal acids and secretions); adherence to epithelial cells, particularly the epithelial cells of the gastrointestinal tract; microbicidal or microbiostatic activity or effect toward pathogenic bacteria; anticarcinogenic activity; immune modulation activity, particularly immune enhancement; modulatory activity toward the endogenous flora; enhanced urogenital tract health; antiseptic activity in or around wounds and enhanced would healing; reduction in diarrhea; reduction in allergic reactions; reduction in neonatal necrotizing enterocolitis; reduction in inflammatory bowel disease; and reduction in intestinal permeability. The probiotics can be prokaryotes, eukaryotes, or archaebacteria. Examples of suitable probiotics include yeasts such as *Saccharomyces, Debaromyces, Candida, Pichia* and *Torulopsis*, moulds such as *Aspergillus, Rhizopus, Mucor*, and *Penicillium* and *Torulopsis* and bacteria such as the genera *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*. In preferred embodiments, the probiotics comprise at least one of any suitable strain or subspecies of *Bacillus*.

"Shampoo" refers to a composition that is applied to the hair or coat of an animal, and optionally scrubbing and/or otherwise dispersing the shampoo throughout the animal's fur or hair in the presence of added water, for use in disinfecting, deodorizing, cleansing, conditioning, and moisturizing the hair or fur;

"Cleansing" refers to the ability of a shampoo to remove dirt and other extraneous or foreign matter from the skin or coat of an animal;

"Conditioning" refers to the ability of a shampoo to provide a soft feel to the coat, and provide hairs that lay flat and are easily combed;

"Moisturizing" refers to the ability of a shampoo to minimize a drying effect a detergent has on the skin or coat of an animal;

The present invention provides a probiotic-containing animal shampoo and methods of using a probiotic-containing animal shampoo for cleansing an animal, reducing odor in an animal and for supporting digestive health in an animal after the animal orally ingests the probiotic during regular grooming activities. In addition to containing at least one probiotic, the shampoo preferably contains environmentally friendly cleaners, moisturizers and conditioners for deep cleaning of the animal's fur coat or hair coat while promoting healing of rough, flakey, oily, or irritated skin.

Preferably, the probiotic shampoo comprises about 1% to about 20% by weight of at least one or more types of probiotics based on the total weight of the entire shampoo composition. Preferably the probiotic-containing shampoos comprises about 10% or more of one or more types of probiotics by weight of probiotics based on the total weight of the entire shampoo composition. Preferably the probiotic-containing shampoos comprises about 5%, 6%, 7%, 8%, 9%, 10% 11%, 12%, 13%, 14%, 15% or more of one or more types of probiotics by weight of probiotics based on the total weight of the entire shampoo the probiotic shampoo of the invention comprises blends of probiotics of different types. Preferably the probiotic shampoo of the invention comprises one or more probiotics of a subspecies of a *Bacillus*.

Preferably the probiotic-containing shampoo of the invention does not include harsh chemicals or chemicals that may irritate the animal upon ingestion. Chemicals that are preferably not included in the probiotic animal shampoo of the invention include, but are not limited to, sulfates, synthetic perfumes or dyes, fatty acid based soaps, sodium lauryl sulfate, polyethylene glycol or other ethoxylated surfactants, propylene glycol, EDTA or any animal-derived products. Animal derived products commonly found in shampoos include, but are not limited to, biotin, lecithin and keratin.

Preferably the probiotic-containing shampoo comprises about 20% to 70% by weight of one or more mild surfactants or detergents based on the weight of the total composition of the shampoo. Preferably the probiotic-containing shampoo comprises about 40% to 60% by weight of one or more mild surfactants or detergents based on the weight of the total composition of the shampoo. Surfactants and detergents serve as cleansing agents amongst other functions. The cleansing agents used in the shampoos of the present invention are used in relatively large amounts. These agents are generally supplied commercially as aqueous solutions and the amounts of cleansing agent used is described as the amount of the commercially supplied solution. Alternatively, given the present teaching, a chemist skilled in the art can prepare and use surfactants independently. Examples of preferred commercially available surfactants include PLANTAPON SF manufactured, for example, by BASF Corporation, (Florham Park, N.J.). Preferably the surfactants used in the composition of the invention are free of betaine.

Preferably the probiotic shampoo comprises moisturizing agents that soften and condition skin and fur or hair coats of animals. Suitable moisturizing agents for use in the shampoo may be identified by those skilled in the art given the present teaching and include lipid layer enhancers such mixtures of alkyl glucosides and fatty acid glyceryl esters such as a combination of coco-glucoside and glyceryl oleate e.g., LAMESOFT PO-65, (BASF Corporation, Florham Park, N.J.). Moisturizing agents may be used at a total concentration of between about 0% and about 20%, by weight based on the weight of the shampoo composition, and preferably between about 1% and about 10% by weight. These materials may also serve dual purposes such as functioning as lipid bilayer enhancers for surfactant based cleansers, and enhancing viscosity in sulfate-free systems.

Preferably the probiotic shampoo comprises small amounts of one or more non-synthetic, naturally-derived, ingestible perfumes such as lavender oil, tea tree oil and cedarwood oil. The word "perfume" as used herein, refers to an ingredient that serves to mask any undesirable odors of other components of a composition of the present invention, and/or provide an appealing odor. Suitable fragrances will become apparent to those skilled in the art. Natural perfumes are generally relatively potent chemicals and require only small amounts, e.g., about 0.01% to about 2% by weight based on the total weight of the shampoo composition, and preferably about 0.05% to about 1%, to achieve the intended effect.

Compositions of the present invention may optionally include a number of other additives in order to provide improved and/or additional properties or features, to the extent such additives do not detrimentally affect the composition to an extent that would make it unsuitable for its intended purpose. Examples of such additives include foam boosters, fragrances, viscosity modifiers, coat shining agents, pearlizing agents, thickening agents, dyes, preservatives and preferably biocompatible, low toxicity preservatives such as KATHON CG/ICP (the Dow Chemical Company), and pH balancers such as citric acid.

Probiotic-containing shampoos of the present invention can be prepared using techniques within the skill of those in the art. The various ingredients may be combined in any suitable manner. The compositions contain added water as a diluent generally about 25% to about 75% (and preferably about 35% to about 50%) by weight based on the total weight of the entire shampoo composition. The water is generally deionized or distilled, or is otherwise relatively pure water, in order to avoid adding unknown ingredients to the composition that might affect the properties of the medicated shampoos of the present invention.

The invention provides a method of orally administering probiotics to an animal comprising contacting the animal's fur or hair with a shampoo that comprises at least one probiotic, wherein the animal subsequently orally self-grooms its fur or hair and thereby orally ingests the probiotic deposited by the shampoo.

The invention also provides a method of supporting digestion in an animal comprising contacting the animal's fur or hair with a shampoo that comprises at least one probiotic, wherein the animal subsequently orally self-grooms its fur or hair and thereby orally ingests the probiotic deposited by the shampoo. The ingested probiotics support digestion in the animal.

The invention further provides a method for reducing odor associated with animal's fur or hair comprising contacting the animal's fur or hair with a shampoo that comprises at least one probiotic.

In accordance with the invention, "contacting" the shampoo with the animal's fur or hair includes shampooing an animal's hair or fur as is known in the art. After rinsing the shampoo from the animal's fur or hair, a therapeutically effective amount of the probiotics contained in the shampoo substantially remain deposited on the hair or fur of the animal. The term "therapeutically effective amount" as used herein is intended to cover an amount that, upon usual grooming by the animal, will be ingested un a quantity sufficient to improve the digestive health of the animal.

EXAMPLES

Example 1—Observations of Improved Digestion in Animals Washed with a Probiotic-Containing Shampoo of the Invention A probiotic-containing shampoo of the invention was prepared having the following formulation I:

TABLE 1

Probiotic-containing Shampoo of Formulation 1

| Ingredient | % by Weight of total Composition |
|---|---|
| Water (diluent) | 36.4 |
| Citric Acid FG (pH balance) | 0.20 |
| PLANTAPON SF (surfactant) See Table 2 | 50.00 |
| Lavender Oil (perfume) | 0.15 |
| Tea Tree Oil (perfume) | 0.05 |
| Cedarwood Oil (perfume) | 0.03 |
| LAMESOFT PO-65 * | 3.00 |
| LAVVAN 2A Concentrate (10×) Probiotic blend | 10.00 |
| KATHON CG ICP** (preservative) | 0.05 |

*Mixture of coco-glucoside and glyceryl oleate.
**KATHON CG/ICP and KATHON CG/ICP II preservatives contain the same type and level of active ingredients (A.I.)—a mixture of two isothiazolinones identified by the IUPAC system of nomenclature as 5-chloro-2-methyl-4-isothiazolin-3-one and 2-methyl-4-isothiazolin-3-one.

TABLE 2

Formulation of PLANTAPON SF (BASF Corporation)

| Ingredient | CAS # | Target (wt %) |
|---|---|---|
| Aqua | 7732-18-5 | >40-60 |
| Glycerin | 56-81-5 | >8-10 |
| Laurel Glucoside | 110615-47-9 | >5-15 |
| Sodium Cocoamphoacetate | 61 | >10-20 |
| Sodium Cococyl Glutamate | | <5 |
| Sodium Lauryl glucose carboxylate | 383178-66-33 | <5 |

Examples

Example 1

A seven-year old female Bulldog mix with chronic stomach and digestive issues and ongoing skin allergies and hypersensitivity was shampooed with a probiotic-containing pet shampoo of Formulation 1 also known by its registered trademarked name, PETSUDS®. The Bulldog mix was shampooed once every 2-weeks for a 4-month period. In the days following initial shampooing, the owner noted positive improvements in both the pet's digestive health and bowel movements. This improvement continued the entire 4-month period of the study. Because of the benefits realized, the owner has continued use of PETSUDS® after study completion. The owner also noted within a couple days following initial shampooing, all skin issues had resolved, and the pet's fur had become soft and shiny. This observation continued the entire 4-month period of the study. Because of the benefits realized, the owner has continued use of PETSUDS® after study completion.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of orally administering probiotics to an animal comprising contacting the animal's fur or hair with a shampoo that comprises at least one probiotic, wherein the animal subsequently orally self-grooms its fur or hair and thereby orally ingests the probiotic deposited by the shampoo.

2. The method of claim 1, wherein the animal is a dog or cat.

3. The method of claim 1, wherein the shampoo comprises at least one surfactant.

4. The method of claim 1, wherein the shampoo comprises at least one moisturizer.

5. The method of claim 1, wherein the shampoo comprises at least one non-synthetic, naturally derived, ingestible perfume.

6. The method of claim 1, wherein the shampoo comprises at least one surfactant, at least one moisturizer and at least one non-synthetic, naturally derived, ingestible perfume.

7. The method of claim 1, wherein the shampoo does not comprise sulfates, synthetic perfumes, dyes, fatty acid-based soaps, sodium lauryl sulfate, polyethylene glycol, ethoxylated surfactants, propylene glycol, EDTA or any animal-derived products.

8. A method of supporting digestion in an animal comprising contacting the animal's fur or hair with a shampoo that comprises at least one probiotic, wherein the animal subsequently orally self-grooms its fur or hair and thereby orally ingests the probiotic deposited by the shampoo and wherein the ingested probiotics support digestion in the animal.

9. The method of claim 8, wherein the animal is a dog or cat.

10. The method of claim 8, wherein the shampoo comprises at least one surfactant.

11. The method of claim 8, wherein the shampoo comprises at least one moisturizer.

12. The method of claim 8, wherein the shampoo comprises at least one non-synthetic, naturally derived, ingestible perfume.

13. The method of claim 8, wherein the shampoo comprises at least one surfactant, at least one moisturizer and at least one non-synthetic, naturally derived, ingestible perfume.

14. The method of claim 8, wherein the shampoo does not comprise sulfates, synthetic perfumes, dyes, fatty acid-based soaps, sodium lauryl sulfate, polyethylene glycol, ethoxylated surfactants, propylene glycol, EDTA or any animal-derived products.

* * * * *

UNITED STATES PATENT AND TRADEMARK OFFICE
CERTIFICATE OF CORRECTION

PATENT NO.       : 10,111,829 B2
APPLICATION NO.  : 15/910275
DATED            : October 30, 2018
INVENTOR(S)      : Shawn E. Seitz Page 1 of 1

It is certified that error appears in the above-identified patent and that said Letters Patent is hereby corrected as shown below:

On the Title Page

Under Assignee: Please delete "Alpha Pet Tech, Inc." and insert the correct name of the Assignee
-- Alpha Tech Pet, Inc. --.

Signed and Sealed this
Twelfth Day of March, 2019

Andrei Iancu
*Director of the United States Patent and Trademark Office*